United States Patent
Vierstra et al.

(10) Patent No.: US 6,455,759 B1
(45) Date of Patent: Sep. 24, 2002

(54) EXPRESSION OF MULTIPLE PROTEINS IN TRANSGENIC PLANTS

(75) Inventors: Richard D. Vierstra; Joseph M. Walker, both of Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/488,270

(22) Filed: Jan. 20, 2000

(51) Int. Cl.⁷ ................ A01H 1/00; A01H 11/00; C12N 15/82; C12N 15/87

(52) U.S. Cl. ............... 800/288; 800/278; 800/295

(58) Field of Search ................ 800/278, 295, 800/288; 435/419; 536/23.1, 23.4

(56) References Cited

U.S. PATENT DOCUMENTS 5,773,705 A * 6/1998 Vierstra et al. ............ 800/250

OTHER PUBLICATIONS

S. Van Nocker et al., Proc. Natl. Acad. Sci, USA, "Cloning and characterization of a 20–k Da ubiquitin carrier protein from wheat that catalyzes multiubiquitin chain formation in vitro," Nov. 1991, vol. 88, pp. 10297–10301.*

D. Hondred et al., Plant Physiology, "Use of ubiquitin fusions to augment protein expression in transgenic plants," Feb. 1999, vol. 119, pp. 713–723.*

R.D. Vierstra, Grant Application, "Development of vectors for the enhanced production of proteins in transgenic plants," 1992, pp. 1–23.*

D. Hondred et al., Biotechnology, "Novel applications of the ubiquitin–dependent proteolytic pathway in plant genetic engineering," 1992, 3: 147–151.*

K.M. Davies, Accession CAA48140, Aug. 1992.*

* cited by examiner

Primary Examiner—Deborah Crouch
Assistant Examiner—Joseph Woitach
(74) Attorney, Agent, or Firm—Quarles & Brady LLP (57) ABSTRACT

A method is disclosed for the production of multiple proteins in transgenic plants. A DNA construct for introduction into plants includes a provision to express a fusion protein of two proteins of interest joined by a linking domain including plant ubiquitin. When the fusion protein is produced in the cells of a transgenic plant transformed with the DNA construction, native enzymes present in plant cells cleave the fusion protein to release both proteins of interest into the cells of the transgenic plant. Since the proteins are produced from the same fusion protein, the initial quantities of the proteins in the cells of the plant are approximately equal.

15 Claims, 3 Drawing Sheets

EXPRESSION OF MULTIPLE PROTEINS IN TRANSGENIC PLANTS

STATEMENT REGARDING FEDERALLY SPONSORED RESEARCH OR DEVELOPMENT

This invention was made with United States government support awarded by the following agency: DOE DE-FC05-92OR22072. The government may have certain rights in this invention.

CROSS-REFERENCE TO RELATED APPLICATIONS

Not applicable.

BACKGROUND OF THE INVENTION

In the art of plant genetics, it has now become common practice to create genetically engineered plants, referred to as transgenic plants, which have stably inserted into their chromosomes one or more foreign gene constructions intended to express a novel or foreign protein in the transgenic plants. Techniques exist to insert genes into plant cells and to regenerate whole fertile transgenic plants from such cells. For several important commercial crop species, transgenic seeds are commercially available and are widely planted and harvested.

The most common techniques currently used for creating plant transformation vectors for plant transformations are based on manipulation and construction of the genetic material in bacterial cells followed by the transfer of the genetic materials from the bacterial cells into plant cells. As most commonly practiced, DNA incorporating a protein coding region for the protein of interest is inserted into a plant expression vector which usually includes a promoter and a transcription termination, or polyadenylation sequence, both of which work in plant cells. The combination of a promoter, protein coding sequence, and a polyadenylation sequence is referred to here as a chimeric gene construction or a plant expression cassette. The plant expression vector often also includes a selectable marker gene, or a gene that confers resistance to a chemical selection agent such as an antibiotic or herbicide. Use of such a selectable marker permits transformed plant cells to be selected from among non-transformed plant cells due to the ability of the transformed plant cells to withstand application of the chemical selection agent to the cells.

Sometimes it is desired that a transgenic plant be constructed that carries more than one foreign gene construction in its genome for more than one gene of interest. If plants are to be altered in their fundamental biochemical characteristics, insertion or alteration of a cascade of enzymes may be needed. While it is possible to incorporate more than one expression cassette into the same plant expression vector, doing so is often not easy or convenient. If two gene cassettes are in the same vector and each includes the same plant promoter or the same polyadenylation sequence, a phenomenon called homologous recombination can occur in the bacterial host which can result in deletion of all of the DNA in the vector which lies in between the two copies of the same promoter. Because there are a limited number of plant promoters known to the art, and since each promoter has different expression characteristics, using two promoters for difference gene cassettes in the same vector can result in different patterns of gene expression for genes that are intended to work in tandem. An alternative approach is to genetically engineer a plant to carry a first inserted gene, called then a transgene, and then to re-engineer the engineered plant to receive a second genetic construction. This approach also has some limitations. First, there are only a few selectable markers known, and one cannot use as a selectable marker in a transformation protocol a marker for which the plant is already resistant. Secondly, when such plant expression cassettes are integrated into the DNA of the plant genome, in general the insertion is at a random location. This gives rise to the so-called "position effect," which is a poorly defined and poorly understood, but widely observed, phenomenon by which the same gene will express at dramatically different levels in different transgenic plants which have the gene inserted in different locations in its genome. Thirdly, the two inserted genes would randomly insert into separate locations in the plant genome, and would thus be genetically unlinked, complicating transfer of the two genes in tandem during plant breeding. Regardless of whether the two inserted genes are introduced at the same time or at two separate times, two genes containing similar sequences in the promoter or polyadenylation signal can adversely affect the activity of each other leading to suppression of both genes, an effect known as co-suppression or gene silencing.

If one wants to engineer a plant to receive a series of enzymes in a cascade intended to produce an end product, one generally wants the enzymes to be produced at relatively similar levels in the cells of the plant. The prior art does not describe convenient methods for achieving such multiple gene expression in plants with comparable or controllable levels of expression among the inserted genes.

Ubiquitin is an abundant protein of 76 amino acids which is present in the cytoplasm and nucleus of all eukaryotic organisms, including plants. Ubiquitin functions as the central component of the ubiquitin-dependent proteolytic pathway, a principle mechanism of amino acid recycling in cells. Ubiquitin is highly conserved and the amino acid sequence of ubiquitin is invariant in all plant species examined so far. Ubiquitin is naturally synthesized as a part of protein fusions which can be polyubiquitins, consisting of multiple ubiquitin monomers in tandem, or ubiquitin extension proteins in which ubiquitin monomers are linked to the amino-terminus of unrelated proteins. The initial fusion proteins produced from such synthesis are naturally processed in vivo to release functional ubiquitin monomers and functional extensions. The enzymes responsible for this activity are known as ubiquitin-specific proteases or UBPs. UBPs are highly specific for ubiquitin and will remove almost any peptide appended by a peptide bond to the carboxyl terminus of ubiquitin, except when proline is the first amino acid of the linked protein at the carboxyl terminus.

Because of its highly stable structure and the natural occurrence of ubiquitin fusions, fusions based on ubiquitin have been previously described as a method to augment the accumulation of unstable or poorly expressed proteins in plants. U.S. Pat. No. 5,773,705 describes a system for using a ubiquitin fusion protein strategy for improving the expression of some proteins in plants.

BRIEF SUMMARY OF THE INVENTION

The present invention is summarized in that a transgenic plant includes an artificial genetic construction which includes, 5' to 3', a promoter operable in plants, a protein coding sequence, and a polyadenylation sequence. The protein coding sequence encodes the expression of a chimeric fusion protein which includes the complete amino acid sequence of at least two proteins of interest joined by a ubiquitin linking domain, the ubiquitin linking domain is cleaved under normal physiological conditions in plant cells to release the two proteins of interest.

The present invention is also summarized in a method for making transgenic plants which includes the steps of constructing a plant gene expression cassette including a promoter operable in plants and a polyadenylation sequence operable in plants, the promoter and the polyadenylation sequence operably connected to a protein coding sequence encoding a fusion protein made up of at least two proteins of interest connected by a ubiquitin linking domain, and transforming the plant gene cassette into a plant such that progeny of the plant produces the two proteins of interest in stoichiometric levels.

It is another aspect of the present invention in that a method is described for the expression of multiple proteins in stoichiometric levels in transgenic plants.

Other object advantages and features will become apparent from the following specification when taken in conjunction with the accompanying drawings.

DETAILED DESCRIPTION OF THE INVENTION

As described here, it is possible to construct a plant expression cassette operable in a transgenic plant, and for that plant expression cassette to encode only a single protein coding sequence, yet still achieve the stoichiometric accumulation of multiple proteins in the transgenic plant. This is accomplished through the stratagem of the plant expression cassette including a protein coding sequence which encodes a fusion protein formed of more than one protein of interest, each pair of proteins of interest being joined together in the fusion protein by a linkage domain based on the sequence of the ubiquitin protein. When the protein coding sequence is expressed in the cells of the host plant, the large fusion protein is expressed. Then the ubiquitin linkage domains of the fusion protein are cleaved by ubiquitin-specific enzymes naturally present in the cells of the plant, this cleavage releasing each of the proteins of interest into the cytosol of the plant cell in approximately equal levels. To facilitate cleavage of the proper proteins in vivo in the plant, it is preferred that the ubiquitin linkage domain include a single ubiquitin head region flanked by two ubiquitin tail regions, one tail at the normal location at the carboxyl terminus of the head region, and another located at the amino terminus of the head region. The second amino terminus tail region facilitates proper release of the upstream protein of interest in a form that retains maximum stability for the upstream protein.

An observation that contributed to the scientific basis for the stratagem used here was the elucidation of the molecular organization of the Bovine Viral Diarrhea Virus (BVDV). The BVDV natively has a rather novel genetic arrangement, in which two viral components are transcribed as a single RNA, which is translated into a fusion protein of two polypeptides joined by a ubiquitin monomer preceded by an additional 14 amino acids from the carboxyl terminus of ubiquitin. The resulting polyprotein is then cleaved in an infected host by indigenous ubiquitin-specific proteases (UBPs) in the host to release the two viral proteins and a free ubiquitin monomer, leaving the 14 amino acid ubiquitin sequence attached to the end of the first protein.

It is disclosed here that the same strategy can be used to make multiple foreign proteins in transgenic plants. In summary, DNA sequences encoding two or more proteins of interest are linked in-frame by a DNA sequence encoding a whole ubiquitin monomer preceded by a DNA sequence encoding the last 14 amino acids of ubiquitin. This fused protein coding sequence is then inserted into a plant expression vector capable of expressing an inserted protein coding sequence in a transgenic plant. The plant expression vector is then transformed into a plant, giving rise to progeny transgenic plants carrying the inserted transgene. In the cells of the progeny transgenic plants, the transgene would be expressed, resulting first in the transcription of an mRNA strand, and then the expression of that strand as a polyprotein or fusion protein. The fusion protein would consist of the two proteins of interest joined by a ubiquitin linkage domain, the ubiquitin linkage domain including at least one ubiquitin monomer and preferably also a 14 amino acid predecessor peptide which corresponds to the carboxyl terminal amino acids of native plant ubiquitin. The fusion protein would be immediately proteolytically cleaved by UBPs present in the cells of the progeny plants, releasing both proteins of interest into the cytoplasm of the cells, and also releasing free ubiquitin monomers. The two proteins, and incidently the free ubiquitin monomers, would be created in exactly the same initial molar quantities. Due to differences in protein stability and degradation, the steady state abundance of the proteins if measured in somatic cells would probably never be precisely equal, but the two proteins would have been produced in precise stoichiometric equality in the cells of the plant. As an incidental side effect, one of the two proteins of interest, the one at the amino terminal end of the fusion protein, would also have at its carboxyl terminus the 14 amino acids from ubiquitin.

Figure 1:
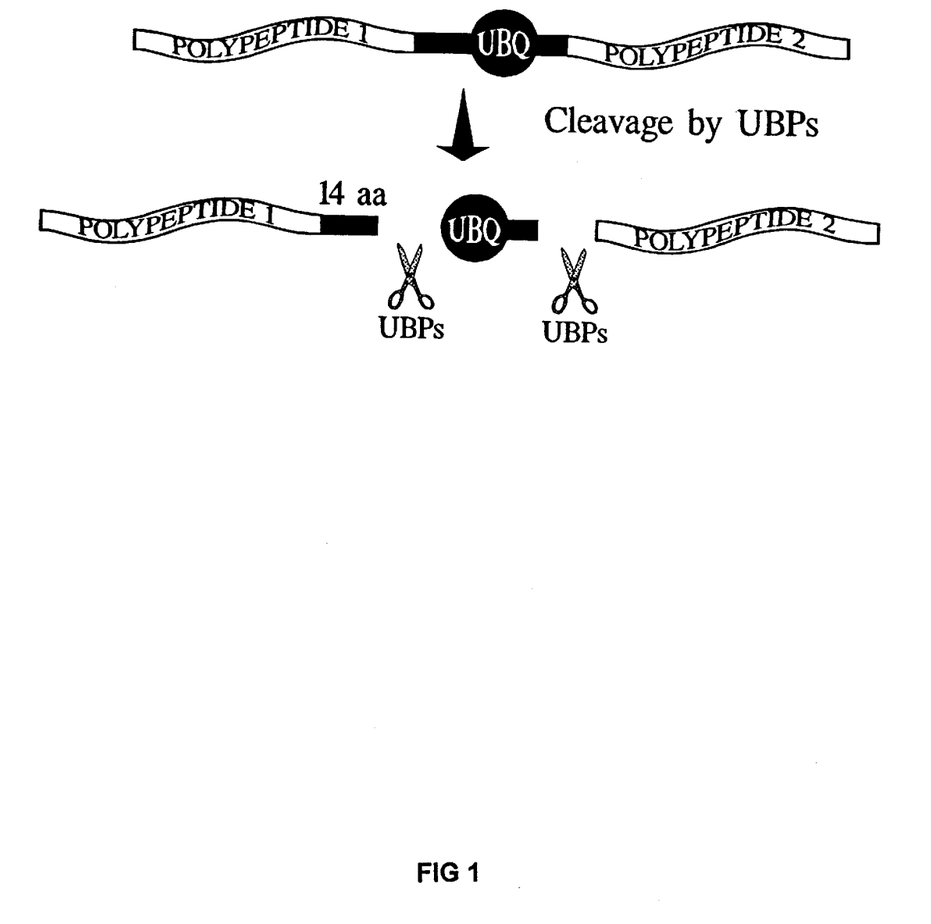
FIG. 1 is a schematic representation of the cleavage of a fusion protein constructed in accordance with the present invention.

The schematic representation in FIG. 1 illustrates this concept. The fusion protein of polypeptide 1 (the first protein of interest) and polypeptide 2 (the second protein of interest) is interrupted by a linkage region illustrated by a ball labeled UBQ and arms extending in each direction. The ball is the ubiquitin head region and the arm to the right is a ubiquitin tail, so that the combination of the two is a complete ubiquitin monomer. The arm to the left is the upstream additional ubiquitin tail region. The proteolytic cleavage action of the UBP enzymes is represented in the illustration by scissors which cleave the fusion protein immediately upstream of the ubiquitin head region and immediately downstream of the complete ubiquitin monomer. The 14 amino acid upstream ubiquitin tail region remains on the carboxyl terminus of the upstream protein of interest labeled polypeptide 1.

While at its simplest, the concept here is to produce two proteins in roughly equal molar amounts, this concept is not limited to two proteins or to equality. One can simply increase the length of the fusion protein by adding another ubiquitin linkage region and another protein of interest to make a third protein, again in stoichiometric equality with the first two. Another alternative would be that the third protein could be another copy of one of the first two proteins to produce one of the two proteins of interest in quantities approximating twice the levels of the first protein. This logic can be continued indefinitely for the number of proteins and their relative proportions, being limited only by the size of the DNA which can be inserted into the transgenic plant and by the length of the mRNA transcript and protein that can be reliably expressed in the plant of interest.

Since, as far as is known, all plants have exactly the same 76 amino acid ubiquitin sequence, and since all plants absolutely require the presence of UBP enzymes to operate their protein recycling capabilities, the approach described here will work in all higher green plants. While the work described below was performed in tobacco, simply due to the fact that tobacco is a relatively convenient plant to genetically engineer, there is absolutely nothing unique in the biochemistry or genetics of tobacco relevant to this technology as compared with any other higher plant.

It is also envisioned that limited alterations can be made to the native plant ubiquitin protein sequence. Of particular interest, it is specifically envisioned, and may be preferred for some applications, to substitute an arginine residue at amino acid position 48 in the ubiquitin sequence to substitute for the native lysine. This substitution precludes the use of the ubiquitin linkage domain from serving as a site for the formation of a multi-ubiquitin chain. The lysine at residue 48 in native ubiquitin has been shown to be the site for polymerization of additional ubiquitins during formation of such multi-ubiquitin chains which are associated with protein degradation. By the use of the term "ubiquitin" in this application, it is meant to refer to both the native ubiquitin sequence as found in the AtUBQ11 gene (Callis et al., *Genetics* 139:921–939 (1995), also set forth in SEQ ID NO:2 below), and the same sequence with a lysine at residue 48, as well as other conservative amino acid substitutions which might be made to the native plant sequence resulting in equivalent protein domains. At a nucleotide level, it is preferred that the native plant coding sequence for ubiquitin be used, with or without the substitution for the lysine48, but it is specifically envisioned that other changes to DNA sequence can be made to result in protein coding sequences which would still result in the expression of a protein which functions as a ubiquitin does in plant systems.

While the approach of Agrobacterium-mediated plant transformation is used in the working examples described here, any other plant transformation technique would be equally adapted for use in the present invention. It is now recognized in the art that the method of insertion of an artificial gene into a plant is, for the most part, irrelevant to the later functioning of the gene, referred to as a transgene, in the progeny from that plant. Such transgenes are inherited by progeny through the rules of normal Mendelian inheritance.

The technique of the present invention therefor enables, for the first time, the production of a plurality of foreign proteins in a transgenic plant, with all the proteins being produced in roughly equivalent amounts. This permits transgenic plants to be created with multiple transgenes in a single transformation event from a non-transgenic variety. And, for those instances in which multiple proteins are sought to be produced in a single transgenic plant, it now becomes possible to produced those proteins in predetermined approximate relationships.

Figure 2:
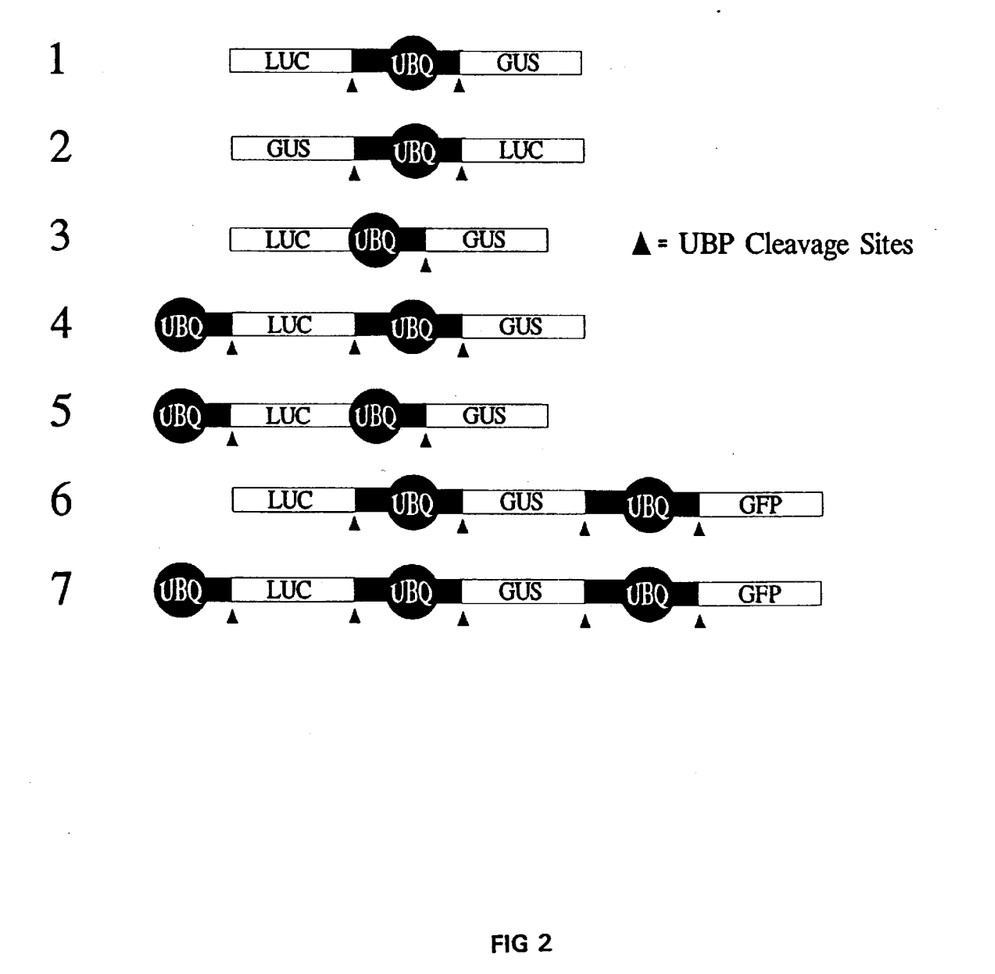
FIG. 2 panels 1–7 are a schematic illustration of several of the chimeric fusions proteins constructed in accordance with the present invention.

FIG. 2 illustrates some of the variations in protein production possible with this technique. Shown in FIG. 2 are seven different variations of a multiple protein gene expression cassette, the variations being labeled 1 through 7. The proteins exemplified in these variations are test proteins which create a phenotype that can readily be assayed. The proteins are the beta-glucuronidase gene (GUS), an enzyme which can be detected by colorimetric assay, luciferase, a protein which emits light in an ATP-dependent reaction, and green flourescent protein (GFP), another flourescent protein. In the illustration of FIG. 2, the cassettes are transcribed, and the resulting mRNAs are then translated, from left to right. Thus whether one considers either the DNA coding regions or the mRNA, or the resulting fusion protein produced, one protein, or its gene, is always in front of at least one other. The proteins are joined by the ubiquitin linkage domain, illustrated as a ball labeled UBQ, an extension from the ball to the right and, sometimes, an extension from the ball to the left. The ball labeled UBQ represents the ubiquitin head domain and the extensions to the left or to the right represent ubiquitin tail domains.

Thus, the DNA coding sequence for alternative 1 includes, 5' to 3', a coding sequence for the LUC protein, a 14 amino acid ubiquitin tail domain, a ubiquitin head domain, another ubiquitin tail domain, and then the coding region for the GUS protein. When this coding sequence is produced in a transgenic plant, a fusion protein is produced containing the LUC protein connected by the ubiquitin linkage domain to the GUS protein. The fusion protein is then proteolytically cleaved by UBP enzymes in the plant cell to release a complete LUC protein with a 14 amino acid ubiquitin tail domain fused to its carboxyl terminus, a complete GUS protein, and one complete ubiquitin protein monomer.

The other alternatives shown in FIG. 2 represent some of the possible variations on this theme. In alternative 2, GUS and LUC coding regions have been reversed. This version will result in the release of the same proteins as did alternative 1, except that there will not be the 14 amino acid ubiquitin tail region appended to the LUC protein. In this case the tail will be on the GUS protein.

In alternative 3, the 14 amino acid ubiquitin tail is omitted from an arrangement otherwise like alternative 1. In this case, neither protein will have the tail appended. While this alternative works, it is thought that the ubiquitin tail region enhances the release of the UBQ from polypeptide 1 by UBPs, and thus alternative 1 is actually preferred over this alternative.

In alternative 4, the arrangement of alternative 1 has been changed to add another complete ubiquitin monomer upstream of the first protein. The addition of this ubiquitin is intended to aid in expression of the entire fusion protein in the plant cells. Since ubiquitin is ubiquitous and abundantly produced in plant cells, it has come to be understood that the ubiquitin protein is one that the protein synthesis machinery of plants can produce with some efficiency. Thus adding the ubiquitin monomer at the amino terminus of the protein can improve the level of production of the fusion protein itself, thus boosting the expression level of all of the proteins in the fusion.

Alternative 5 is similar to alternative 4 except that the ubiquitin tail domain upstream of the ubiquitin domain in the interior of the coding region has been omitted.

Alternatives 6 and 7 are intended to illustrate three protein fusions of LUC, GUS and GFP. In each of these arrangements, there are two linkage domains, each with a complete ubiquitin monomer preceded by an extra tail domain. Alternative 7 adds a complete ubiquitin monomer at the amino terminus of the fusion protein, a feature not included in Alternative 6.

EXAMPLES Construction of LUC-U3'-UBQ-GUS Fusion

A DNA coding sequence for a fusion of luciferase, a ubiquitin linkage domain and beta-glucuronidase, as illustrated in Alternative 1 of FIG. 2, was constructed using standard cloning techniques using PCR oligonucleotide primers to generate the protein fusion junctions. To assemble an expression cassette operable in plants, the following components were joined together in order 5' to 3': a PCR fragment containing the CaMV 35S promoter (Barton er al. *Plant Physiol.* 85:1103–1109 (1987)), the 39-bp of the 5' upstream untranslated region from alfalfa mosaic virus (Gehrke et al. *Biochemistry*, 22:5157–5164, 1983), the full length coding region for the luciferase protein from pAB14016LBS (de Wet et al. *Mol. Cell Biol.* 7:725–737 (1983)), followed in frame by the last 42-bp of the third repeat of the AtUBQ11 gene (Callis et al. *Genetics*, 139:921–939, 1995), followed in frame by the first 10-bp of the same ubiquitin coding region. All these elements were generated from a luciferase expression vector using the standard M13-20 primer:

5'-GTAAAACGACGGCCAGT-3', and the antisense primer:

5'-AGACTCGCATACCACCGCGGAGACGGAG-
GACCAAGTGAAGAGTAGAC TCCTTCAATTTG-
GACTTTCCGCC-3'.

The luciferase coding region in this vector had been previously modified to contain a translationally silent KasI site 39-bp downstream from the start codon. The ubiquitin coding sequence had been previously modified to contain a translationally silent BglII site 10-bp downstream from its start codon and a translationally silent SacII site 5-bp upstream from the carboxy terminal glycine. The resulting PCR fragment was cloned into an EcoRV digest of the vector pBluescriptII KS (Stratagene) and then excised as a KpnI/BglII fragment. The KpnI/BglII fragment thus produced, CaMV35S-AMV-LUC-U3'-UBQ, was cloned into a KpnI/BglII digest of an expression vector containing the same CaMV35S-AMV cassette followed by the third repeat of the AtUBQ11 coding region translationally fused to the GUS-coding region and the nopaline synthase transcriptional terminator from the plasmid pCMC1100 (McCabe et al. *Biotechnology* 6:923–926 (1988)). The GUS-coding region had been previously modified to contain a translationally silent XhoI site 31-bp downstream from the start codon. The completed expression cassette for the fusion protein was then cloned into the binary vector BIN19 (Clontech) as a KpnI/SalI fragment.

The entire sequence of the expression cassette for this construction is set forth in SEQ ID NO:1 below. In SEQ ID NO:1, base pairs numbered 1 to 452 are the CaMV35S promoter beginning at the KpnI site. Following that are the 39 base pairs of the AMV untranslated leader sequence.

The protein coding region for the fusion protein begins at base pair 490 and continues on to 4216. Bases 490 through 2140 contain the coding sequence for the luciferase gene (amino acids 1 through 550 in the protein). The next 42 bases (2141 to 2182) are the coding region for a ubiquitin tail region (amino acids 551 through 564). Then follows the coding region for a complete ubiquitin monomer from bases 2183 through 2410, amino acids 565 through 640. The coding region for the second protein of interest, in this case GUS, begins at base 2411 and continues on through base 4216, amino acids 641 through 1242. The remaining bases in the sequence, bases 4217 to 4544, are a nopaline synthase polyadenylation sequence ending in a SalI site.

Plant Transformations

The completed BIN19 plasmid was then introduced directly into *Agrobacterium tumefaciens* strain LBA4404, which was then used to transform tobacco (*Nicotiana tabacum* cv Xanthi) leaf disks using the method of Cherry et al. *Plant Cell* 5:565–575 (1993). Cells in culture were selected for kanamycin resistance and stably transformed kanamycin resistant plants were recovered. Transgenic plants were transferred to soil and grown to maturity in a greenhouse.

Enzyme Extractions and Analysis

In order to evaluate the enzyme levels in the cells of the plants, total proteins were extracted from the youngest expanded leaves of transformed plants. The total soluble protein in the samples was measured by the Bradford method (Bradford et al. *Anal. Biochem.* 72:248–254 (1976)). Total soluble protein was extracted by grinding transgenic plant tissue in 25 mM Tris-phosphate (pH7.8), 20 mM sodium metabisulfite, 2 mM 1,2-diaminecyclohexane-N,N,N',N'-tetraacetic acid, 10% (v/v) glycerol, and 1% (v/v) Triton X-100. For GUS activity measurement, a fluorometric assay was used with 4-methylumbelliferyl β-D-glucuronide as the substrate. LUC activity was determined using a chemiluminescence assay system from Promega Corporation.

Immunoblot Analysis

Proteins were separated by SDS-PAGE, electrotransferred to immobilon-P membrane (Millipore), and then subjected to immunoblot assay as previously described in van Nocker et al. *J. Biol. Chem.* 268:24766–24773 (1993). Rabbit polyclonal antibodies were prepared against partially purified GUS protein purchased from Sigma which was further purified by Mono-Q ion-exchange chromatography (Pharmacia) before injection into a New Zealand White rabbit as a one-to-one mixture of Freund's adjuvant and antigen following a standard course of intradermal injections. LUC antibodies were purchased from Promega Corporation. The immunoreactive proteins were identified with alkaline phosphatase-coupled IgGs (Kirkegaard and Perry Laboratories).

Results

Transgenic tobacco plants have been recovered transformed with a transgene expressing a fusion protein of LUC and GUS with the ubiquitin linkage domain placed between them (Alternative 1 of FIG. 2). Analysis of the resulting proteins confirmed that free forms of the proteins were detected for both proteins in the tissues of the plants.

This experiment has been repeated in Arabidopsis and again both proteins were produced and detected in free form.

Figure 3:
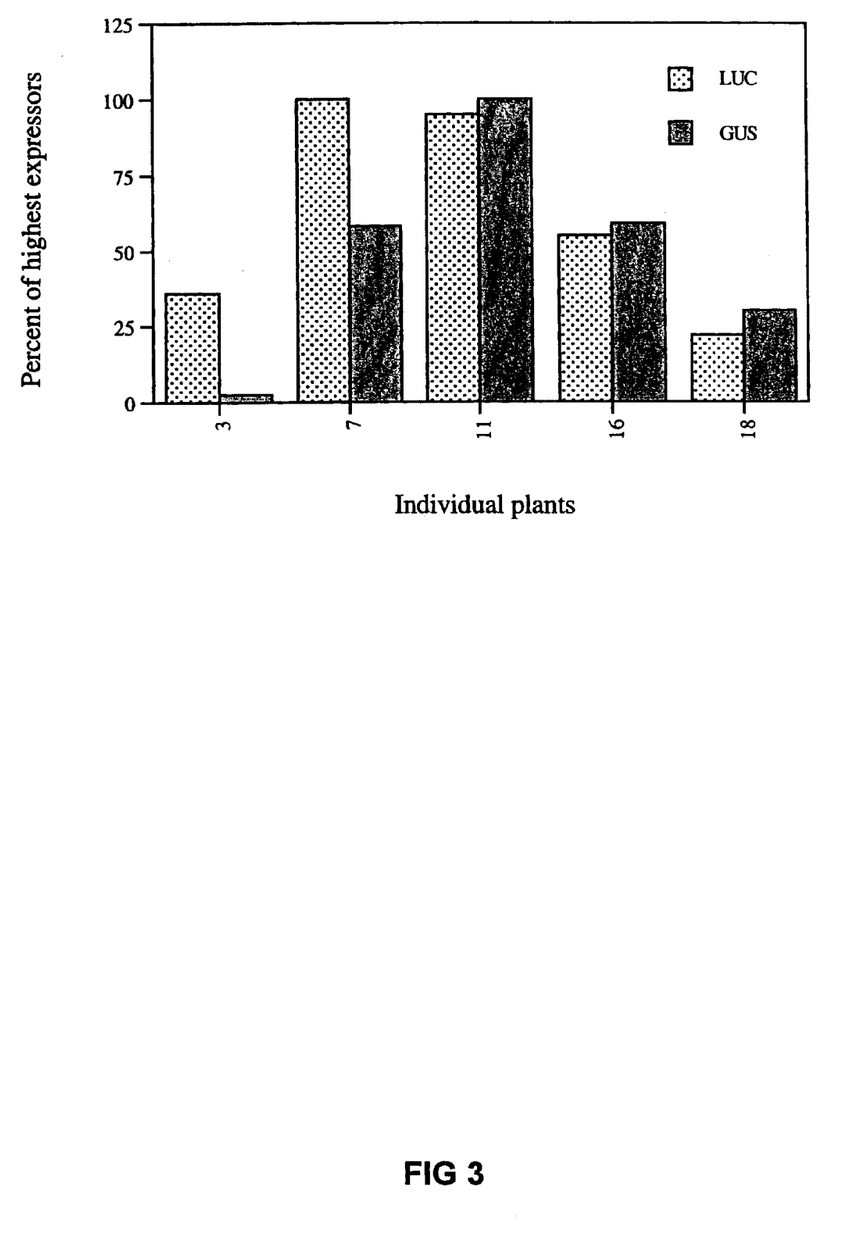
FIG. 3 is a graphical representation of some of the results from the example below.

Transformation of the vector alternative 1 into tobacco plants resulted in plants expressing both luciferase and beta-glucuronidase. Analysis by SDS-PAGE and western blotting showed proteins corresponding to the full length beta-glucuronidase and the luciferase protein with the added 14 amino acid luciferase tail. Quantitative assays on five independently transformed plants revealed levels of the two reporter enzymes which are similar. The results are presented in the form of bar graphs in FIG. 3.

I/We claim:

1. A transgenic angiosperm plant comprising a DNA construction inserted into the genome of the plant, the DNA construction comprising 5' to 3':
   a promoter operable in plant cells;
   a coding region encoding a fusion protein, the fusion protein comprising in a common reading frame, in order:
      a coding region for a first protein of interest;
      a coding region for a plant ubiquitin monomer; and
      a coding region for second protein of interest;
   a transcriptional terminator operable in plants,
   le;2qthe coding region encoding the fusion protein effective in the cells of the transgenic plant to result in translation of the fusion protein in the cells of the plant, the fusion protein being cleaved at the ubiquitin monomer by enzymes present in the cells of the plant separating the first and second proteins of interest from each other in the cells of the transgenic plant, neither the first nor the second proteins of interest being ubiquitin.

2. Seeds of the plant of claim 1 which carry the DNA construction in their genome.

3. The plant as claimed in claim 1 wherein the coding sequence for the plant ubiquitin monomer encodes an arginine at amino acid position 48 substituted for the lysine present at that position in native plant ubiquitin sequence.

4. A transgenic angiosperm plant comprising in its genome a DNA construction, the DNA construction comprising 5' to 3':
   a promoter operable in plant cells;
   a coding region encoding a fusion protein, the fusion protein comprising in a common reading fame, in order:
      a region encoding a first protein of interest;
      a region encoding a plant ubiquitin tail region consisting essentially of the carboxyl terminus 14 amino acids of plant ubiquitin;
      a region encoding an entire plant ubiquitin monomer; and
      a region encoding a second protein of interest;
   a transcriptional terminator operable in plants,
   the coding region encoding a fusion protein effective in the cells of the transgenic plant to produce the fusion protein in the cells of the plant, the fusion protein being cleaved by enzymes present in the cells of the plant at one end of the ubiquitin tail region to separate the first and second proteins of interest from each other in the cells of the transgenic plant, neither the first nor the second protein of interest being ubiquitin.

5. Seeds of the plant of claim 4 which carry the DNA construction in their genome.

6. The plant as claimed in claim 4 where in the region encoding the plant ubiquitin monomer encodes an arginine at amino acid position 48 substituted for the lysine residue at that position in native plant ubiquitin sequence.

7. An artificial DNA construct comprising 5' to 3':
   a promoter operable in plant cells;
   a coding region encoding a fusion protein, the fusion protein comprising in a common reading frame, in order,
      a coding region for a first protein of interest;
      a coding region for a plant ubiquitin monomer; and
      a coding region for second protein of interest;
   a transcriptional terminator operable in plants,
   the coding region encoding the fusion protein effective when the DNA construct is transformed into the genome of the cells of a transgenic angiosperm plant to produce the fusion protein in the cells of the plant, the fusion protein being cleaved at the ubiquitin monomer by enzymes present in the cells of the plant to separate the first and second proteins of interest in the cells of the transgenic plant, neither of the first or second proteins of interest from each other being ubiquitin.

8. The DNA construct of claim 7 wherein the fusion protein also includes at the end of the first protein of interest a coding region encoding a tail domain from plant ubiquitin, the tail domain consisting essentially of the carboxyl terminus 14 amino acids of plant ubiquitin.

9. The DNA construct of claim 7 wherein the coding region for ubiquitin includes a substitution of a codon for the amino acid arginine for the codon for the amino acid lysine present at position 48 in the native ubiquitin sequence.

10. A method for producing at least two proteins in a transgenic angiosperm plant comprising the steps of
    (a) making a DNA construction which includes
       a promoter operable in plant cells;
       a coding region encoding a fusion protein, the fusion protein comprising in a common reading frame, in order,
          a coding region for a first protein of interest;
          a coding region for a plant ubiquitin monomer; and
          a coding region for second protein of interest;
       a transcriptional terminator operable in plants, neither the first nor the second protein of interest being a ubiquitin;
    (b) transforming the DNA construction of step (a) into the genome of a plant cell and recovering a transgenic plant therefrom; and
    (c) cultivating the transgenic plant to maturity such that the fusion protein is produced in the cells of the plant, the fusion protein being cleaved at the ubiquitin monomer by enzymes in the cells of the plant separating the two proteins of interest from each other in the cells of the transgenic plant.

11. The method of claim 10 wherein the fusion protein also includes a ubiquitin tail domain at the end of the first protein of interest, the tail domain consisting essentially of the carboxyl terminus 14 amino acids of plant ubiquitin.

12. The method of claim 10 wherein the coding region for the plant ubiquitin includes a substitution of an arginine residue at amino acid position 48 for the lysine residue present at that position in native plant ubiquitin.

13. A method for producing at least two proteins in a transgenic angiosperm plant comprising the steps of
    (a) providing a seed which comprises in its genome an artificial DNA construction which includes
       a promoter operable in plant cells;
       a coding region encoding a fusion protein, the fusion protein comprising in a common reading frame, in order,
          a coding region for a first protein of interest;
          a coding region for a plant ubiquitin monomer; and
          a coding region for second protein of interest;
       a transcriptional terminator operable in plants, neither the first nor the second protein of interest being ubiquitin;

(b) growing the seed of step (a) into a transgenic plant under conditions such that the fusion protein is produced in the cells of the transgenic plant, the fusion protein being cleaved at the ubiquitin monomer by enzymes in the cells of the transgenic plant to release the two proteins of interest into the cells of the transgenic plant.

14. The method of claim 13 wherein the fusion protein also includes a ubiquitin tail domain consisting essentially of the carboxyl terminus 14 amino acids of plant ubiquitin at the end of the first protein of interest.

15. The method of claim 14 wherein the coding region for the plant ubiquitin includes a substitution of an arginine residue at amino acid position 48 for the lysine residue present at that position in native plant ubiquitin.

* * * * *

SEQUENCE LISTING

<160> NUMBER OF SEQ ID NOS: 4

<210> SEQ ID NO 1
<211> LENGTH: 4544
<212> TYPE: DNA
<213> ORGANISM: Artificial Sequence
<220> FEATURE:
<221> NAME/KEY: CDS
<222> LOCATION: (491)..(4216)
<223> OTHER INFORMATION: Description of Artificial Sequence:Fusion
      Protein Expression Cassette

<400> SEQUENCE: 1

```
ggtaccgggc cccggccggc tagcgtcgag gaacatggtg gagcacgaca ctctcgtcta      60
ctccaagaat atcaaagata cagtctcaga agaccaaagg gctattgaga cttttcaaca     120
aagggtaata tcgggaaacc tcctcggatt ccattgccca gctatctgtc acttcatcaa     180
aaggacagta gaaaggaag gtggcaccta caaatgccat cattgcgata aaggaaaggc     240
tatcgttcaa gatgcctctg ccgacagtgg tcccaaagat ggaccccac ccacgaggag     300 catcgtggaa aagaagacg ttccaaccac gtcttcaaag caagtggatt gatgtgatat     360
ctccactgac gtaagggatg acgcacaatc ccactatcct tcgcaagacc cttcctctat     420
ataaggaagt tcatttcatt tggagaggac caagcttttt attttaatt ttctttcaaa     480
```

```
tacttccacc atg gaa gac gcc aaa aac ata aag aaa ggc ccg gcg cca            529
            Met Glu Asp Ala Lys Asn Ile Lys Lys Gly Pro Ala Pro
            1               5                   10 ttc tat cct cta gag gat gga acc gct gga gag caa ctg cat aag gct           577
Phe Tyr Pro Leu Glu Asp Gly Thr Ala Gly Glu Gln Leu His Lys Ala
    15                  20                  25 atg aag aga tac gcc ctg gtt cct gga aca att gct ttt aca gat gca           625
Met Lys Arg Tyr Ala Leu Val Pro Gly Thr Ile Ala Phe Thr Asp Ala
30                  35                  40                  45 cat atc gag gtg aac atc acg tac gcg gaa tac ttc gaa atg tcc gtt           673
His Ile Glu Val Asn Ile Thr Tyr Ala Glu Tyr Phe Glu Met Ser Val
                50                  55                  60 cgg ttg gca gaa gct atg aaa cga tat ggg ctg aat aca aat cac aga           721
Arg Leu Ala Glu Ala Met Lys Arg Tyr Gly Leu Asn Thr Asn His Arg
            65                  70                  75 atc gtc gta tgc agt gaa aac tct ctt caa ttc ttt atg ccg gtg ttg           769
Ile Val Val Cys Ser Glu Asn Ser Leu Gln Phe Phe Met Pro Val Leu
        80                  85                  90 ggc gcg tta ttt atc gga gtt gca gtt gcg ccc gcg aac gac att tat           817
Gly Ala Leu Phe Ile Gly Val Ala Val Ala Pro Ala Asn Asp Ile Tyr
    95                  100                 105 aat gaa cgt gaa ttg ctc aac agt atg aac att tcg cag cct acc gta           865
Asn Glu Arg Glu Leu Leu Asn Ser Met Asn Ile Ser Gln Pro Thr Val
110                 115                 120                 125 gtg ttt gtt tcc aaa aag ggg ttg caa aaa att ttg aac gtg caa aaa           913
Val Phe Val Ser Lys Lys Gly Leu Gln Lys Ile Leu Asn Val Gln Lys
                130                 135                 140 aaa tta cca ata atc cag aaa att att atc atg gat tct aaa acg gat           961
Lys Leu Pro Ile Ile Gln Lys Ile Ile Ile Met Asp Ser Lys Thr Asp
            145                 150                 155 tac cag gga ttt cag tcg atg tac acg ttc gtc aca tct cat cta cct          1009
Tyr Gln Gly Phe Gln Ser Met Tyr Thr Phe Val Thr Ser His Leu Pro
        160                 165                 170 ccc ggt ttt aat gaa tac gat ttt gta cca gag tcc ttt gat cgt gac          1057
Pro Gly Phe Asn Glu Tyr Asp Phe Val Pro Glu Ser Phe Asp Arg Asp
```

|  |  |  |  |  |  |  |  |  |  |  |  |  |  |  |  |
|---|---|---|---|---|---|---|---|---|---|---|---|---|---|---|---|
|  |  | 175 |  |  |  |  | 180 |  |  |  |  | 185 |  |  |  |

```
aaa aca att gca ctg ata atg aat tcc tct gga tct act ggg tta cct      1105
Lys Thr Ile Ala Leu Ile Met Asn Ser Ser Gly Ser Thr Gly Leu Pro
190             195                 200                 205 aag ggt gtg gcc ctt ccg cat aga act gcc tgc gtc aga ttc tcg cat      1153
Lys Gly Val Ala Leu Pro His Arg Thr Ala Cys Val Arg Phe Ser His
                210                 215                 220 gcc aga gat cct att ttt ggc aat caa atc att ccg gat act gcg att      1201
Ala Arg Asp Pro Ile Phe Gly Asn Gln Ile Ile Pro Asp Thr Ala Ile
                225                 230                 235 tta agt gtt gtt cca ttc cat cac ggt ttt gga atg ttt act aca ctc      1249
Leu Ser Val Val Pro Phe His His Gly Phe Gly Met Phe Thr Thr Leu
                240                 245                 250 gga tat ttg ata tgt gga ttt cga gtc gtc tta atg tat aga ttt gaa      1297
Gly Tyr Leu Ile Cys Gly Phe Arg Val Val Leu Met Tyr Arg Phe Glu
            255                 260                 265 gaa gag ctg ttt tta cga tcc ctt cag gat tac aaa att caa agt gcg      1345
Glu Glu Leu Phe Leu Arg Ser Leu Gln Asp Tyr Lys Ile Gln Ser Ala
270             275                 280                 285 ttg cta gta cca acc cta ttt tca ttc ttc gcc aaa agc act ctg att      1393
Leu Leu Val Pro Thr Leu Phe Ser Phe Phe Ala Lys Ser Thr Leu Ile
                290                 295                 300 gac aaa tac gat tta tct aat tta cac gaa att gct tct ggg ggc gca      1441
Asp Lys Tyr Asp Leu Ser Asn Leu His Glu Ile Ala Ser Gly Gly Ala
                305                 310                 315 cct ctt tcg aaa gaa gtc ggg gaa gcg gtt gca aaa cgc ttc cat ctt      1489
Pro Leu Ser Lys Glu Val Gly Glu Ala Val Ala Lys Arg Phe His Leu
                320                 325                 330 cca ggg ata cga caa gga tat ggg ctc act gag act aca tca gct att      1537
Pro Gly Ile Arg Gln Gly Tyr Gly Leu Thr Glu Thr Thr Ser Ala Ile
            335                 340                 345 ctg att aca ccc gag ggg gat gat aaa ccg ggc gcg gtc ggt aaa gtt      1585
Leu Ile Thr Pro Glu Gly Asp Asp Lys Pro Gly Ala Val Gly Lys Val
350             355                 360                 365 gtt cca ttt ttt gaa gcg aag gtt gtg gat ctg gat acc ggg aaa acg      1633
Val Pro Phe Phe Glu Ala Lys Val Val Asp Leu Asp Thr Gly Lys Thr
                370                 375                 380 ctg ggc gtt aat cag aga ggc gaa tta tgt gtc aga gga cct atg att      1681
Leu Gly Val Asn Gln Arg Gly Glu Leu Cys Val Arg Gly Pro Met Ile
                385                 390                 395 atg tcc ggt tat gta aac aat ccg gaa gcg acc aac gcc ttg att gac      1729
Met Ser Gly Tyr Val Asn Asn Pro Glu Ala Thr Asn Ala Leu Ile Asp
                400                 405                 410 aag gat gga tgg cta cat tct gga gac ata gct tac tgg gac gaa gac      1777
Lys Asp Gly Trp Leu His Ser Gly Asp Ile Ala Tyr Trp Asp Glu Asp
            415                 420                 425 gaa cac ttc ttc ata gtt gac cgc ttg aag tct tta att aaa tac aaa      1825
Glu His Phe Phe Ile Val Asp Arg Leu Lys Ser Leu Ile Lys Tyr Lys
430             435                 440                 445 gga tac cag gtg gcc ccc gct gaa ttg gaa tcg ata ttg tta caa cac      1873
Gly Tyr Gln Val Ala Pro Ala Glu Leu Glu Ser Ile Leu Leu Gln His
                450                 455                 460 ccc aac atc ttc gac gcg ggc gtg gca ggt ctt ccc gac gat gac gcc      1921
Pro Asn Ile Phe Asp Ala Gly Val Ala Gly Leu Pro Asp Asp Asp Ala
                465                 470                 475 ggt gaa ctt ccc gcc gcc gtt gtt gtt ttg gag cac gga aag acg atg      1969
Gly Glu Leu Pro Ala Ala Val Val Val Leu Glu His Gly Lys Thr Met
                480                 485                 490 acg gaa aaa gag atc gtg gat tac gtc gcc agt caa gta aca acc gcg      2017
```

-continued

```

Thr Glu Lys Glu Ile Val Asp Tyr Val Ala Ser Gln Val Thr Thr Ala
    495                 500                 505 aaa aag ttg cgc gga gga gtt gtg ttt gtg gac gaa gta ccg aaa ggt     2065
Lys Lys Leu Arg Gly Gly Val Val Phe Val Asp Glu Val Pro Lys Gly
510                 515                 520                 525 ctt acc gga aaa ctc gac gca aga aaa atc aga gag atc ctc ata aag     2113
Leu Thr Gly Lys Leu Asp Ala Arg Lys Ile Arg Glu Ile Leu Ile Lys
                530                 535                 540 gcc aag aag ggc gga aag tcc aaa ttg aag gag tct act ctt cac ttg     2161
Ala Lys Lys Gly Gly Lys Ser Lys Leu Lys Glu Ser Thr Leu His Leu
            545                 550                 555 gtc ctc cgt ctc cgc ggt ggt atg cag atc ttc gta aag act ttg acc     2209
Val Leu Arg Leu Arg Gly Gly Met Gln Ile Phe Val Lys Thr Leu Thr
        560                 565                 570 gga aag acc atc act ctt gaa gtt gag agc tcc gac acc att gat aac     2257
Gly Lys Thr Ile Thr Leu Glu Val Glu Ser Ser Asp Thr Ile Asp Asn
    575                 580                 585 gtg aag gct aag atc cag gac aag gaa ggc att cct ccg gac cag cag     2305
Val Lys Ala Lys Ile Gln Asp Lys Glu Gly Ile Pro Pro Asp Gln Gln
590                 595                 600                 605 cgt ctc atc ttc gct gga aag cag ctt gag gat gga cgt act ttg gcc     2353
Arg Leu Ile Phe Ala Gly Lys Gln Leu Glu Asp Gly Arg Thr Leu Ala
                610                 615                 620 gac tac aac atc cag aag gag tct act ctt cac ttg gtc ctc cgt ctc     2401
Asp Tyr Asn Ile Gln Lys Glu Ser Thr Leu His Leu Val Leu Arg Leu
            625                 630                 635 cgc ggt ggt atg tta cgt cct gta gaa acc cca act cga gaa atc aaa     2449
Arg Gly Gly Met Leu Arg Pro Val Glu Thr Pro Thr Arg Glu Ile Lys
        640                 645                 650 aaa ctc gac ggc ctg tgg gca ttc agt ctg gat cgc gaa aac tgt gga     2497
Lys Leu Asp Gly Leu Trp Ala Phe Ser Leu Asp Arg Glu Asn Cys Gly
    655                 660                 665 att gat cag cgt tgg tgg gaa agc gcg tta caa gaa agc cgg gca att     2545
Ile Asp Gln Arg Trp Trp Glu Ser Ala Leu Gln Glu Ser Arg Ala Ile
670                 675                 680                 685 gct gtg cca ggc agt ttt aac gat cag ttc gcc gat gca gat att cgt     2593
Ala Val Pro Gly Ser Phe Asn Asp Gln Phe Ala Asp Ala Asp Ile Arg
                690                 695                 700 aat tat gcg ggc aac gtc tgg tat cag cgc gaa gtc ttt ata ccg aaa     2641
Asn Tyr Ala Gly Asn Val Trp Tyr Gln Arg Glu Val Phe Ile Pro Lys
            705                 710                 715 ggt tgg gca ggc cag cgt atc gtg ctg cgt ttc gat gcg gtc act cat     2689
Gly Trp Ala Gly Gln Arg Ile Val Leu Arg Phe Asp Ala Val Thr His
        720                 725                 730 tac ggc aaa gtg tgg gtc aat aat cag gaa gtg atg gag cat cag ggc     2737
Tyr Gly Lys Val Trp Val Asn Asn Gln Glu Val Met Glu His Gln Gly
    735                 740                 745 ggc tat acg cca ttt gaa gcc gat gtc acg ccg tat gtt att gcc ggg     2785
Gly Tyr Thr Pro Phe Glu Ala Asp Val Thr Pro Tyr Val Ile Ala Gly
750                 755                 760                 765 aaa agt gta cgt atc acc gtt tgt gtg aac aac gaa ctg aac tgg cag     2833
Lys Ser Val Arg Ile Thr Val Cys Val Asn Asn Glu Leu Asn Trp Gln
                770                 775                 780 act atc ccg ccg gga atg gtg att acc gac gaa aac ggc aag aaa aag     2881
Thr Ile Pro Pro Gly Met Val Ile Thr Asp Glu Asn Gly Lys Lys Lys
            785                 790                 795 cag tct tac ttc cat gat ttc ttt aac tat gcc gga atc cat cgc agc     2929
Gln Ser Tyr Phe His Asp Phe Phe Asn Tyr Ala Gly Ile His Arg Ser
        800                 805                 810
```

-continued

```
gta atg ctc tac acc acg ccg aac acc tgg gtg gac gat atc acc gtg    2977
Val Met Leu Tyr Thr Thr Pro Asn Thr Trp Val Asp Asp Ile Thr Val
    815                 820                 825 gtg acg cat gtc gcg caa gac tgt aac cac gcg tct gtt gac tgg cag    3025
Val Thr His Val Ala Gln Asp Cys Asn His Ala Ser Val Asp Trp Gln
830                 835                 840                 845 gtg gtg gcc aat ggt gat gtc agc gtt gaa ctg cgt gat gcg gat caa    3073
Val Val Ala Asn Gly Asp Val Ser Val Glu Leu Arg Asp Ala Asp Gln
                850                 855                 860 cag gtg gtt gca act gga caa ggc act agc ggg act ttg caa gtg gtg    3121
Gln Val Val Ala Thr Gly Gln Gly Thr Ser Gly Thr Leu Gln Val Val
            865                 870                 875 aat ccg cac ctc tgg caa ccg ggt gaa ggt tat ctc tat gaa ctg tgc    3169
Asn Pro His Leu Trp Gln Pro Gly Glu Gly Tyr Leu Tyr Glu Leu Cys
        880                 885                 890 gtc aca gcc aaa agc cag aca gag tgt gat atc tac ccg ctt cgc gtc    3217
Val Thr Ala Lys Ser Gln Thr Glu Cys Asp Ile Tyr Pro Leu Arg Val
    895                 900                 905 ggc atc cgg tca gtg gca gtg aag ggc gaa cag ttc ctg att aac cac    3265
Gly Ile Arg Ser Val Ala Val Lys Gly Glu Gln Phe Leu Ile Asn His
910                 915                 920                 925 aaa ccg ttc tac ttt act ggc ttt ggt cgt cat gaa gat gcg gac tta    3313
Lys Pro Phe Tyr Phe Thr Gly Phe Gly Arg His Glu Asp Ala Asp Leu
                930                 935                 940 cgt ggc aaa gga ttc gat aac gtg ctg atg gtg cac gac cac gca tta    3361
Arg Gly Lys Gly Phe Asp Asn Val Leu Met Val His Asp His Ala Leu
            945                 950                 955 atg gac tgg att ggg gcc aac tcc tac cgt acc tcg cat tac cct tac    3409
Met Asp Trp Ile Gly Ala Asn Ser Tyr Arg Thr Ser His Tyr Pro Tyr
        960                 965                 970 gct gaa gag atg ctc gac tgg gca gat gaa cat ggc atc gtg gtg att    3457
Ala Glu Glu Met Leu Asp Trp Ala Asp Glu His Gly Ile Val Val Ile
    975                 980                 985 gat gaa act gct gct gtc ggc ttt aac ctc tct tta ggc att ggt ttc    3505
Asp Glu Thr Ala Ala Val Gly Phe Asn Leu Ser Leu Gly Ile Gly Phe
990                 995                 1000                1005 gaa gcg ggc aac aag ccg aaa gaa ctg tac agc gaa gag gca gtc aac    3553
Glu Ala Gly Asn Lys Pro Lys Glu Leu Tyr Ser Glu Glu Ala Val Asn
                1010                1015                1020 ggg gaa act cag caa gcg cac tta cag gcg att aaa gag ctg ata gcg    3601
Gly Glu Thr Gln Gln Ala His Leu Gln Ala Ile Lys Glu Leu Ile Ala
            1025                1030                1035 cgt gac aaa aac cac cca agc gtg gtg atg tgg agt att gcc aac gaa    3649
Arg Asp Lys Asn His Pro Ser Val Val Met Trp Ser Ile Ala Asn Glu
        1040                1045                1050 ccg gat acc cgt ccg caa gtg cac ggg aat att tcg cca ctg gcg gaa    3697
Pro Asp Thr Arg Pro Gln Val His Gly Asn Ile Ser Pro Leu Ala Glu
    1055                1060                1065 gca acg cgt aaa ctc gac ccg acg cgt ccg atc acc tgc gtc aat gta    3745
Ala Thr Arg Lys Leu Asp Pro Thr Arg Pro Ile Thr Cys Val Asn Val
1070                1075                1080                1085 atg ttc tgc gac gct cac acc gat acc atc agc gat ctc ttt gat gtg    3793
Met Phe Cys Asp Ala His Thr Asp Thr Ile Ser Asp Leu Phe Asp Val
                1090                1095                1100 ctg tgc ctg aac cgt tat tac gga tgg tat gtc caa agc ggc gat ttg    3841
Leu Cys Leu Asn Arg Tyr Tyr Gly Trp Tyr Val Gln Ser Gly Asp Leu
            1105                1110                1115 gaa acg gca gag aag gta ctg gaa aaa gaa ctt ctg gcc tgg cag gag    3889
Glu Thr Ala Glu Lys Val Leu Glu Lys Glu Leu Leu Ala Trp Gln Glu
        1120                1125                1130
```

-continued

```
aaa ctg cat cag ccg att atc atc acc gaa tac ggc gtg gat acg tta         3937
Lys Leu His Gln Pro Ile Ile Ile Thr Glu Tyr Gly Val Asp Thr Leu
    1135            1140                1145 gcc ggg ctg cac tca atg tac acc gac atg tgg agt gaa gag tat cag         3985
Ala Gly Leu His Ser Met Tyr Thr Asp Met Trp Ser Glu Glu Tyr Gln
1150                1155                1160                1165 tgt gca tgg ctg gat atg tat cac cgc gtc ttt gat cgc gtc agc gcc         4033
Cys Ala Trp Leu Asp Met Tyr His Arg Val Phe Asp Arg Val Ser Ala
                1170                1175                1180 gtc gtc ggt gaa cag gta tgg aat ttc gcc gat ttt gcg acc tcg caa         4081
Val Val Gly Glu Gln Val Trp Asn Phe Ala Asp Phe Ala Thr Ser Gln
            1185                1190                1195 ggc ata ttg cgc gtt ggc ggt aac aag aaa ggg atc ttc act cgc gac         4129
Gly Ile Leu Arg Val Gly Gly Asn Lys Lys Gly Ile Phe Thr Arg Asp
        1200                1205                1210 cgc aaa ccg aag tcg gcg gct ttt ctg ctg caa aaa cgc tgg act ggc         4177
Arg Lys Pro Lys Ser Ala Ala Phe Leu Leu Gln Lys Arg Trp Thr Gly
    1215                1220                1225 atg aac ttc ggt gaa aaa ccg cag cag gga ggc aaa caa tgaatcaaca          4226
Met Asn Phe Gly Glu Lys Pro Gln Gln Gly Gly Lys Gln
1230                1235                1240 actctcctgg cgcaccatcg tcggctacag cctcggtggg aattcctgca gggatccccg       4286
gggatcgttc aaacatttgg caataaagtt tcttaagatt gaatcctgtt gccggtcttg       4346
cgatgattat catataattt ctgttgaatt acgttaagca tgtaataatt aacatgtaat       4406
gcatgacgtt atttatgaga tgggttttat gattagagtc ccgcaattat acatttaata      4466
cgcgatagaa aacaaaatat agcgcgacta ggataaatta tcgcgcgcgg tgtcatctat      4526
gttactagat ccgtcgac                                                     4544
```

<210> SEQ ID NO 2
<211> LENGTH: 1242
<212> TYPE: PRT
<213> ORGANISM: Artificial Sequence
<220> FEATURE:
<223> OTHER INFORMATION: Description of Artificial Sequence:Fusion
      Protein Expression Cassette

<400> SEQUENCE: 2

```
Met Glu Asp Ala Lys Asn Ile Lys Lys Gly Pro Ala Pro Phe Tyr Pro
 1               5                  10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140
```

-continued

```
Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ser Lys Leu Lys Glu Ser Thr Leu His Leu Val Leu Arg
545                 550                 555                 560

Leu Arg Gly Gly Met Gln Ile Phe Val Lys Thr Leu Thr Gly Lys Thr
```

-continued

```
                565                 570                 575
Ile Thr Leu Glu Val Glu Ser Ser Asp Thr Ile Asp Asn Val Lys Ala
                580                 585                 590
Lys Ile Gln Asp Lys Glu Gly Ile Pro Pro Asp Gln Gln Arg Leu Ile
                595                 600                 605
Phe Ala Gly Lys Gln Leu Glu Asp Gly Arg Thr Leu Ala Asp Tyr Asn
610                 615                 620
Ile Gln Lys Glu Ser Thr Leu His Leu Val Leu Arg Leu Arg Gly Gly
625                 630                 635                 640
Met Leu Arg Pro Val Glu Thr Pro Thr Arg Glu Ile Lys Lys Leu Asp
                645                 650                 655
Gly Leu Trp Ala Phe Ser Leu Asp Arg Glu Asn Cys Gly Ile Asp Gln
                660                 665                 670
Arg Trp Trp Glu Ser Ala Leu Gln Glu Ser Arg Ala Ile Ala Val Pro
                675                 680                 685
Gly Ser Phe Asn Asp Gln Phe Ala Asp Ala Asp Ile Arg Asn Tyr Ala
                690                 695                 700
Gly Asn Val Trp Tyr Gln Arg Glu Val Phe Ile Pro Lys Gly Trp Ala
705                 710                 715                 720
Gly Gln Arg Ile Val Leu Arg Phe Asp Ala Val Thr His Tyr Gly Lys
                725                 730                 735
Val Trp Val Asn Asn Gln Glu Val Met Glu His Gln Gly Gly Tyr Thr
                740                 745                 750
Pro Phe Glu Ala Asp Val Thr Pro Tyr Val Ile Ala Gly Lys Ser Val
                755                 760                 765
Arg Ile Thr Val Cys Val Asn Asn Glu Leu Asn Trp Gln Thr Ile Pro
                770                 775                 780
Pro Gly Met Val Ile Thr Asp Glu Asn Gly Lys Lys Lys Gln Ser Tyr
785                 790                 795                 800
Phe His Asp Phe Phe Asn Tyr Ala Gly Ile His Arg Ser Val Met Leu
                805                 810                 815
Tyr Thr Thr Pro Asn Thr Trp Val Asp Asp Ile Thr Val Val Thr His
                820                 825                 830
Val Ala Gln Asp Cys Asn His Ala Ser Val Asp Trp Gln Val Val Ala
                835                 840                 845
Asn Gly Asp Val Ser Val Glu Leu Arg Asp Ala Asp Gln Gln Val Val
850                 855                 860
Ala Thr Gly Gln Gly Thr Ser Gly Thr Leu Gln Val Val Asn Pro His
865                 870                 875                 880
Leu Trp Gln Pro Gly Glu Gly Tyr Leu Tyr Glu Leu Cys Val Thr Ala
                885                 890                 895
Lys Ser Gln Thr Glu Cys Asp Ile Tyr Pro Leu Arg Val Gly Ile Arg
                900                 905                 910
Ser Val Ala Val Lys Gly Glu Gln Phe Leu Ile Asn His Lys Pro Phe
                915                 920                 925
Tyr Phe Thr Gly Phe Gly Arg His Glu Asp Ala Asp Leu Arg Gly Lys
                930                 935                 940
Gly Phe Asp Asn Val Leu Met Val His Asp His Ala Leu Met Asp Trp
945                 950                 955                 960
Ile Gly Ala Asn Ser Tyr Arg Thr Ser His Tyr Pro Tyr Ala Glu Glu
                965                 970                 975
Met Leu Asp Trp Ala Asp Glu His Gly Ile Val Val Ile Asp Glu Thr
                980                 985                 990
```

```
Ala Ala Val Gly Phe Asn Leu Ser Leu Gly Ile Gly Phe Glu Ala Gly
        995                1000                1005
Asn Lys Pro Lys Glu Leu Tyr Ser Glu Ala Val Asn Gly Glu Thr
    1010                1015                1020
Gln Gln Ala His Leu Gln Ala Ile Lys Glu Leu Ile Ala Arg Asp Lys
1025                1030                1035                1040
Asn His Pro Ser Val Val Met Trp Ser Ile Ala Asn Glu Pro Asp Thr
                1045                1050                1055
Arg Pro Gln Val His Gly Asn Ile Ser Pro Leu Ala Glu Ala Thr Arg
            1060                1065                1070
Lys Leu Asp Pro Thr Arg Pro Ile Thr Cys Val Asn Val Met Phe Cys
        1075                1080                1085
Asp Ala His Thr Asp Thr Ile Ser Asp Leu Phe Asp Val Leu Cys Leu
    1090                1095                1100
Asn Arg Tyr Tyr Gly Trp Tyr Val Gln Ser Gly Asp Leu Glu Thr Ala
1105                1110                1115                1120
Glu Lys Val Leu Glu Lys Glu Leu Leu Ala Trp Gln Glu Lys Leu His
                1125                1130                1135
Gln Pro Ile Ile Ile Thr Glu Tyr Gly Val Asp Thr Leu Ala Gly Leu
            1140                1145                1150
His Ser Met Tyr Thr Asp Met Trp Ser Glu Glu Tyr Gln Cys Ala Trp
        1155                1160                1165
Leu Asp Met Tyr His Arg Val Phe Asp Arg Val Ser Ala Val Val Gly
    1170                1175                1180
Glu Gln Val Trp Asn Phe Ala Asp Phe Ala Thr Ser Gln Gly Ile Leu
1185                1190                1195                1200
Arg Val Gly Gly Asn Lys Lys Gly Ile Phe Thr Arg Asp Arg Lys Pro
                1205                1210                1215
Lys Ser Ala Ala Phe Leu Leu Gln Lys Arg Trp Thr Gly Met Asn Phe
            1220                1225                1230
Gly Glu Lys Pro Gln Gln Gly Gly Lys Gln
        1235                1240

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 3
gtaaaacgac ggccagt                                                    17

<210> SEQ ID NO 4
<211> LENGTH: 70
<212> TYPE: DNA
<213> ORGANISM: Artificial Sequence
<220> FEATURE:
<223> OTHER INFORMATION: Description of Artificial Sequence:primer

<400> SEQUENCE: 4
agactcgcat accaccgcgg agacggagga ccaagtgaag agtagactcc ttcaatttgg     60
actttccgcc                                                            70
```